(12) United States Patent
Mori et al.

(10) Patent No.: US 12,071,604 B2
(45) Date of Patent: Aug. 27, 2024

(54) CULTURE VESSEL

(71) Applicant: SCREEN HOLDINGS CO., LTD., Kyoto (JP)

(72) Inventors: Yuki Mori, Kyoto (JP); Hiroki Fujimoto, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 621 days.

(21) Appl. No.: 17/383,197

(22) Filed: Jul. 22, 2021

(65) Prior Publication Data

US 2022/0089988 A1    Mar. 24, 2022

(30) Foreign Application Priority Data

Sep. 23, 2020   (JP) ................. 2020-159011

(51) Int. Cl.
*C12M 1/32* (2006.01)
*C12M 1/00* (2006.01)

(52) U.S. Cl.
CPC ............ *C12M 23/12* (2013.01); *C12M 23/22* (2013.01)

(58) Field of Classification Search
CPC ....... C12M 23/12; C12M 23/22; C12M 41/36
See application file for complete search history.

(56) References Cited

U.S. PATENT DOCUMENTS

| | | | |
|---|---|---|---|
| 9,062,283 B2 | 6/2015 | Woodside et al. |
| 9,261,454 B2 | 2/2016 | Egeler et al. |
| 9,931,633 B2 | 4/2018 | Egeler et al. |

FOREIGN PATENT DOCUMENTS

JP    2016-014974 A    1/2016

*Primary Examiner* — Lydia Edwards
(74) *Attorney, Agent, or Firm* — Rimon P.C.

(57) ABSTRACT

An culture vessel includes one or more recesses, each having a flat bottom surface, and a side surface extending upward from the peripheral edge of the bottom surface and including a rough surface with arithmetic mean roughness of 0.18 μm to 5.0 μm. The rough surface is water repellent and reduces meniscus formation on the peripheral edge of the upper surface of the culture solution. This suppresses a reduction in light amount at the peripheral edges of recesses due to meniscus formation. On the side surfaces of recesses, secondary illumination light is diffused and reflected. This suppresses formation of an image (ghost) of a biological sample by the secondary illumination light. Accordingly, it is possible to suppress a reduction in the amount of light due to meniscus formation in the culture solution and to reduce formation of an image of the biological sample by the secondary illumination light.

9 Claims, 10 Drawing Sheets

CULTURE VESSEL

RELATED APPLICATIONS

This application claims the benefit of Japanese Application No. 2020-159011, filed on Sep. 23, 2020, the disclosure of which is incorporated by reference herein.

BACKGROUND OF THE INVENTION

Field of the Invention

The present invention relates to a culture vessel that is used to hold therein a biological sample together with a culture solution and to observe the biological sample under epi-illumination.

Description of the Background Art

Apparatuses that observe the culture state of cells cultured in a vessel by capturing images of the cells at high resolutions have been known conventionally. For example, Japanese Patent Application Laid-Open No. 2016-14974 describes such a conventional apparatus. The apparatus disclosed in Japanese Patent Application Laid-Open No. 2016-14974 captures images of cells held in a vessel from the underside of the vessel while applying illumination light to the cells from above the vessel.

With this type of apparatus, a well plate with a plurality of wells (recesses) may be used as a vessel for culturing cells. The well plate holds cells in its each well together with a culture solution. At this time, a meniscus is formed on the peripheral edge of the upper surface of the culture solution due to surface tension of the culture solution. That is, the peripheral edge of the upper surface of the culture solution is curved to form a concave shape. In this case, light incident on the peripheral edge of the upper surface of the culture solution is refracted outward due to the effect of a concave lens. Thus, there are problems that the amount of light at the peripheral edges of the wells decreases and accordingly the peripheral edges of the wells become darker in the captured image.

The illumination light incident on the wells includes primary illumination light that travels vertically downward and secondary illumination light that travels diagonally downward. Part of the secondary illumination light enters side surfaces of the wells and is mirror-reflected on the side surfaces. In this case, when the well plate is viewed from the underside, an image of the cells formed by the primary illumination light and an image (ghost) of the cells formed by the aforementioned reflected light of the secondary illumination light appear. Thus, there is a problem that double images of the cells appear.

The present invention has been made in light of such circumstances, and it is an object of the present invention to provide a technique for, when a biological sample such as cells is observed under epi-illumination, suppressing a reduction in the amount of light due to meniscus formation on the surface of the culture solution and preventing an image of the biological sample from being formed by the secondary illumination light.

SUMMARY OF THE INVENTION

In order to solve the problems described above, a first aspect of the present application is a culture vessel for use in holding therein a biological sample together with a culture solution and observing the biological sample under epi-illumination. The culture vessel includes one or a plurality of recesses. The one or a plurality of recesses each have a flat bottom surface, and a side surface extending upward from a peripheral edge of the bottom surface. The side surface includes a rough surface. The rough surface has arithmetic mean roughness greater than or equal to 0.18 µm and less than or equal to 5.0 µm.

A second aspect of the present application is the culture vessel according to the first aspect, in which the rough surface has a plurality of flaws, and the plurality of flaws have widths greater than or equal to 25 µm and less than or equal to 10 µm.

A third aspect of the present application is the culture vessel according to the first or second aspect, in which the plurality of flaws in the rough surface have a flaw spacing greater than or equal to 30 µm and less than or equal to 60 µm.

A fourth aspect of the present application is the culture vessel according to any one of the first to third aspects, in which the rough surface has the arithmetic mean roughness in a longitudinal section.

A fifth aspect of the present application is the culture vessel according to any one of the first to fourth aspects, in which the rough surface has asperities of different sizes distributed at random.

A sixth aspect of the present application is the culture vessel according to any one of the first to fifth aspects, in which the rough surface is distributed all around the side surface.

A seventh aspect of the present application is the culture vessel according to any one of the first to sixth aspects, in which the rough surface is distributed entirely from an upper end of the side surface to a lower end of the side surface.

An eighth aspect of the present application is the culture vessel according to any one of the first to seventh aspects, in which the rough surface is a machined surface formed by sandblasting, grinding using a grinder with abrasive grains or micro-projections, pressing using a mold with projections and depressions, chemical etching, or plasma irradiation.

A ninth aspect of the present application is the culture vessel according to any one of the first to eighth aspects. The culture vessel is a well plate including a plurality of recesses, the plurality of recesses being the one or a plurality of recesses.

According to the first to ninth aspects of the present application, the side surfaces of the recesses in the culture vessel are rough surfaces and water-repellent. This reduces meniscus formation on the peripheral edge of the upper surface of the culture solution. Accordingly, it is possible to suppress a reduction in the amount of light at the peripheral edges of the recesses due to meniscus formation. The secondary illumination light is diffused and reflected on the side surfaces of the recesses. Thus, it is also possible to reduce the possibility that an image (ghost) of the biological sample is formed by the secondary illumination light.

These and other objects, features, aspects and advantages of the present invention will become more apparent from the following detailed description of the present invention when taken in conjunction with the accompanying drawings.

DESCRIPTION OF PREFERRED EMBODIMENT

Hereinafter, a preferable embodiment of the present invention will be described with reference to the drawings.

1. Configuration of Well Plate

Figure 1:
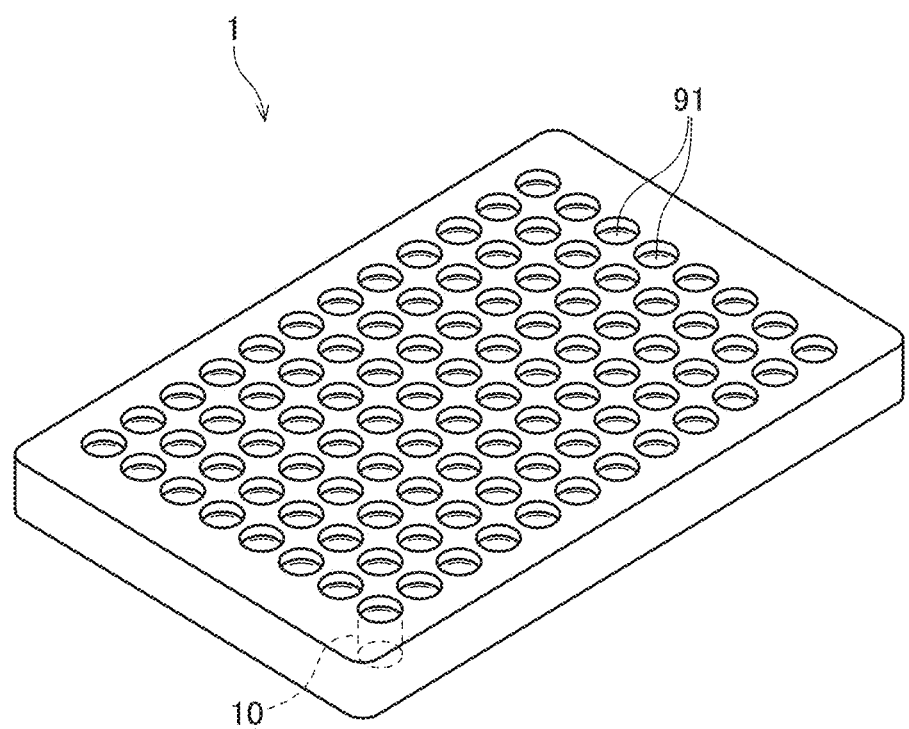
FIG. 1 is a perspective view of a well plate.
Figure 2:
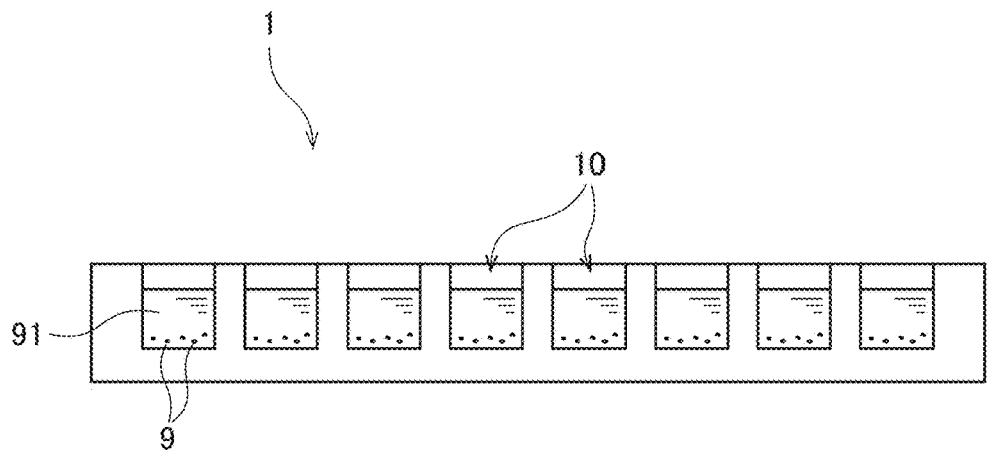
FIG. 2 is a longitudinal sectional view of the well plate.

FIG. 1 is a perspective view of a well plate 1 as one example of a culture vessel. FIG. 2 is a longitudinal sectional view of the well plate 1. The well plate 1 is a substantially plate-like vessel having a plurality of wells (recesses) 10. The well plate 1 may be made of, for example, a transparent resin that passes light. As illustrated in FIG. 1, the wells 10 are arranged regularly in the upper surface of the well plate 1. In the present embodiment, the wells 10 have a circular shape when viewed from above. However, the shape of the wells 10 when viewed from above may be any other shape such as a rectangle.

As illustrated in FIG. 2, each well 10 holds therein a biological sample 9 to be observed, together with a culture solution 91. Thus, the biological sample 9 is cultured in each well 10. The culture solution 91 may, for example, be a Dulbecco's modified Eagle's medium (DMEM), a Roswell park memorial institute medium (RPMI), or physiological saline. The biological sample 9 may be a single cell, or may be a cell cluster (spheroid) formed by a plurality of cells. The biological sample 9 may also be a tissue of a living body, or may be part of the tissue.

Figure 3:
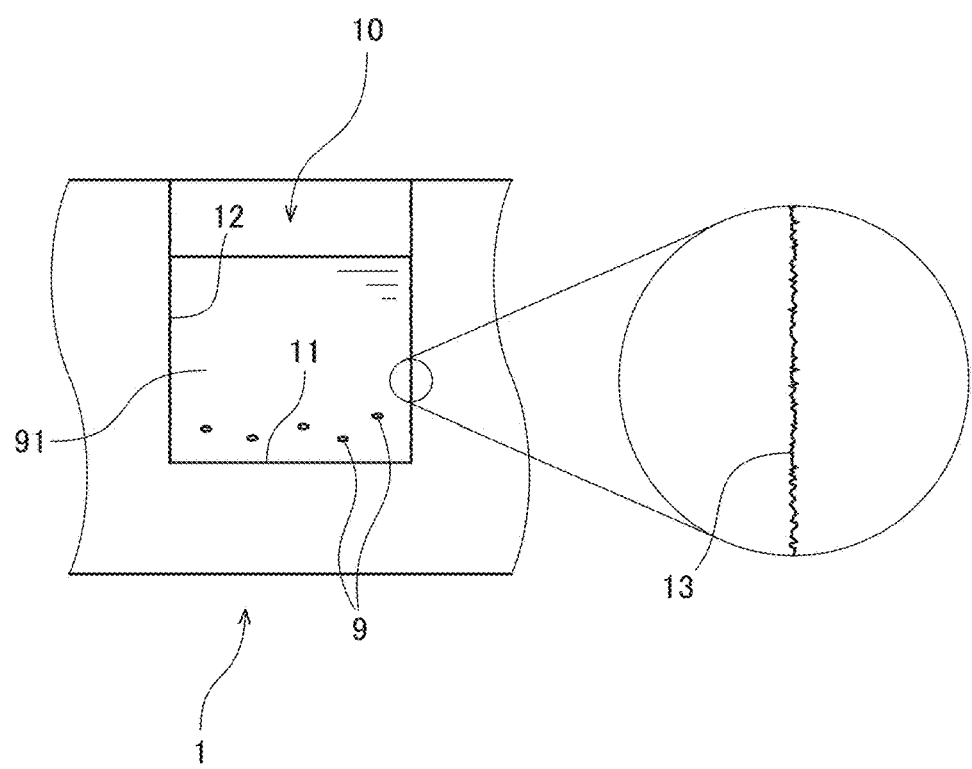
FIG. 3 is a longitudinal sectional view of the vicinity of one well.

FIG. 3 is a longitudinal sectional view of the vicinity of one well 10. As illustrated in FIG. 3, the well 10 has a bottom surface 11 and a side surface 12. The bottom surface 11 is a flat surface that extends perpendicular to the up-down direction. The side surface 12 is a cylinder-like surface that extends upward from the peripheral edge of the bottom surface 11. In order to facilitate mold release during molding of the well plate 1, the side surface 12 may be slightly tapered with increasing diameter toward the top.

The bottom surface 11 of the well 10 is flat. In contrast, the side surface 12 of the well 10 is a rough surface 13 with microscopic asperities as illustrated in enlarged dimensions in FIG. 3. The rough surface 13 may, for example, be a machined surface formed by sandblasting, grinding by a grinder using abrasive grains or micro-projections, pressing using a mold with projections and depressions, chemical etching, or plasma irradiation. The grinder may, for example, be abrasive cloth such as sandpaper, a file, or a mounted wheel.

The rough surface 13 has arithmetic mean roughness (arithmetic mean roughness Ra described by JIS B 0601: 2013) greater than or equal to 0.18 μm and less than or equal to 5.0 μm. By making the surface with such surface roughness, it is possible to favorably achieve both the effect of reducing meniscus formation in the culture solution 91, which will be described later, and the effect of reducing the possibility that an image (ghost) of the biological sample 9 is formed by secondary illumination light, which will be described later.

The asperities on the rough surface 13 may be dotted in both the vertical and horizontal directions, or may be such that asperities extending linearly in the horizontal direction are arranged in stripes in the vertical direction. In either case, the rough surface 13 desirably has arithmetic mean roughness Ra that falls within the aforementioned range in a longitudinal section.

The rough surface 13 according to the present embodiment has asperities located at random. That is, the rough surface 13 may be such that asperities of different sizes within the aforementioned range of arithmetic mean roughness Ra are distributed at random. By so doing, it is possible to increase variations in the viscosity of the culture solution 91 while reducing the possibility of meniscus formation.

The spacing of flaws in the rough surface 13 is desirably greater than or equal to 30 μm and less than or equal to 60 μm. By so doing, it is possible to favorably archive both the effect of reducing meniscus formation in the culture solution 91 and the effect of reducing the possibility that an image (ghost) of the biological sample 9 is formed by the secondary illumination light. In particular, the rough surface 13 desirably has a flaw spacing within the aforementioned range in a longitudinal section.

The flaw spacing will be described here. The flaw spacing refers to an indicator of the interval of peaks in cross-sectional profiles in the vicinity of an arbitrary point. The method of calculating the flaw spacing is as follows. First, a central point in cross-sectional profiles (hereinafter, also referred to as profile line segments) of a predetermined unit length of the rough surface 13 is defined, and for example, the profile line segments are rotated 0 degree, 45 degrees, 90 degrees, and 135 degrees, respectively about the central point to obtain the cross-sectional profiles at every angle. In the cross-sectional profile at each angle, a peak-to-peak distance between every two adjacent peaks, each expressed as a convex-downward-shaped projection, is calculated, and an average value of the peak-to-peak distances is determined as an average peak-to-peak distance. The average peak-to-peak distance is calculated for each angle, and among these calculated average peak-to-peak distances, a smallest average peak-to-peak distance is determined as the flaw spacing according to the present embodiment. The peaks used to calculate the peak-to-peak distances are determined as peak positions that are the lowest (deepest) positions of "valleys (convex-downward-shaped projections)" that cross a height reference line and that is regarded as flaws (i.e., the deepest positions of the valleys described by JIS B 0601:2013). Note that the angles of rotation of the profile line segments are not limited to the aforementioned angles. That is, the number of profile line segments obtained for one central point is not limited to four. Besides, the angles of rotation of the profile line segments do not necessarily have to be constant.

As described above, the rough surface 13 may be formed by adding a plurality of flaws to a smooth surface. In the case where the rough surface 13 has a plurality of flaws as described above, the flaws desirably have widths greater than or equal to 25 μm and less than or equal to 110 μm. By so doing, it is possible to more favorably achieve both the effect of reducing meniscus formation in the culture solution 91 and the effect of reducing the possibility that an image (ghost) of the biological sample 9 is formed by the secondary illumination light.

In the present embodiment, the whole side surface 12 is the aforementioned rough surface 13. That is, the rough surface 13 is distributed all around the side surface 12. The rough surface 13 is also distributed entirely from the lower end of the side surface 12 to the upper end thereof. Alternatively, only part of the side surface 12 may be the aforementioned rough surface 13. It is, however, noted that at least portions of the side surface 12 that come in contact with the culture solution 91 during use of the well plate 1 are desirably the rough surface 13.

2. Configuration of Image Capturing Device

Figure 4:
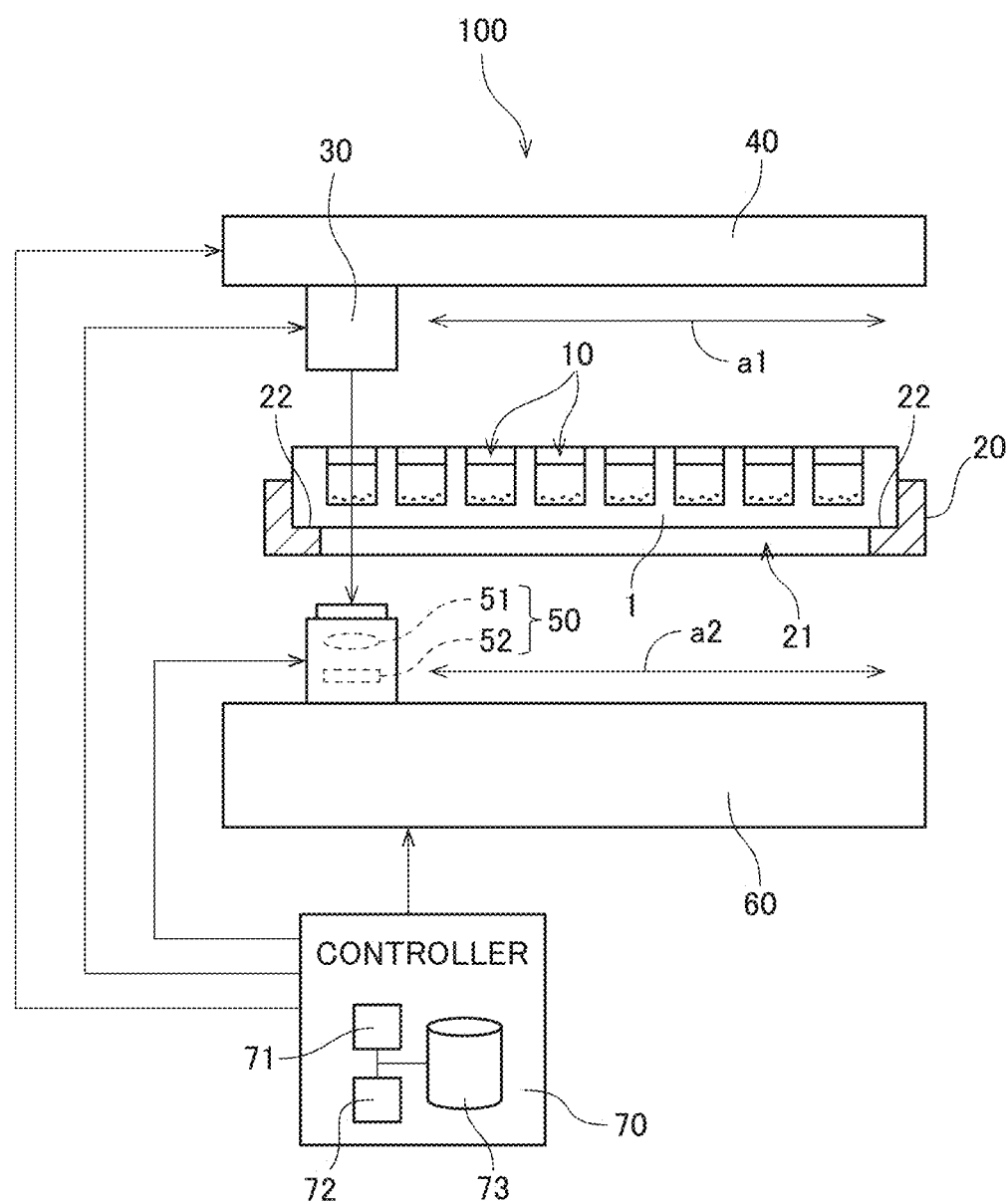
FIG. 4 is an illustration of a configuration of an image capturing device.

Next is a description of an image capturing device 100 for capturing an image of the biological sample 9 with use of the aforementioned well plate 1. FIG. 4 is an illustration of a configuration of the image capturing device 100. The image capturing device 100 is a device that captures an image of the biological sample 9 held in each well 10 of the well plate 1 to generate an image for observation. As illustrated in FIG. 4, the image capturing device 100 according to the present embodiment includes a stage 20, a projector 30, a projector moving mechanism 40, a camera 50, a camera moving mechanism 60, and a controller 70.

The stage 20 is a placement base on which the well plate 1 is held. The position of the stage 20 in the image capturing device 100 is fixed at least during image capture. The stage 20 has a rectangular opening 21 vertically extending therethrough in the center. The stage 20 also has a ring-shaped support surface 22 at the edge of the opening 21. The well plate 1 is fitted in the opening 21 and supported in a horizontal position by the support surface 22. Thus, the upper and lower portions of the wells 10 are exposed without being blocked by the stage 20.

The projector 30 is arranged above the well plate 1 held on the stage 20. The projector 30 includes a light source such as an LED. The light source of the projector 30 emits light while an image of the biological sample 9 is captured. Thus, downward illumination light (epi-illumination) is emitted from the projector 30 toward the well plate 1.

The projector moving mechanism 40 is a mechanism for moving the projector 30 horizontally along the upper surface of the well plate 1 held on the stage 20. For example, the projector moving mechanism 40 may be a mechanism for converting rotational motion of a motor into straight-forward motion via a ball screw. The image capturing device 100 operates the projector moving mechanism 40 to arrange the projector 30 at a position above each well 10 of the well plate 1. In FIG. 4, only one direction indicated by an arrow a1 is illustrated as the direction of travel of the projector 30. However, the projector moving mechanism 40 may move the projector 30 in two directions (the left-right direction and the depth direction in FIG. 4) along the upper surface of the well plate 1.

The camera 50 is arranged below the well plate 1 held on the stage 20. The camera 50 includes an optical system 51 such as a lens and an image sensor 52 such as a CCD or a CMOS. When an image of the biological sample 9 is captured, the projector 30 emits downward illumination light toward some of the wells 10 of the well plate 1, and the camera 50 captures an image of these wells 10 of the well plate 1. In this way, the camera 50 acquires an image of the biological sample 9 in each well 10 as digital data. The captured image is output from the camera 50 to the controller 70.

The camera moving mechanism 60 is a mechanism for moving the camera 50 horizontally along the lower surface of the well plate 1 held on the stage 20. For example the camera moving mechanism 60 may be a mechanism for converting rotational motion of a motor into straight-forward motion via a ball screw. The image capturing device 100 operates the camera moving mechanism 60 to arrange the camera 50 at a position below each well 10 of the well plate 1. In FIG. 4, only one direction indicated by an arrow a2 is illustrated as the direction of travel of the camera 50. However, the camera moving mechanism 60 may move the camera 50 in two directions (the left-right direction and the depth direction in FIG. 4) along the lower surface of the well plate 1.

The projector moving mechanism 40 and the camera moving mechanism 60 described above are driven in synchronization with each other. Accordingly, the projector 30 and the camera 50 are always arranged at the same position when viewed from above. That is, the projector 30 and the camera 50 are moved in the same direction by the same distance, and when the camera 50 is arranged at a position below a given well 10, the projector 30 is always arranged at a position above this well 10.

The controller 70 is a unit for controlling operations of each part of the image capturing device 100. As illustrated in FIG. 4, the controller 70 is configured as a computer that includes a processor 71 such as a CPU, a memory 72 such as a RAM, and a storage such as a hard disk drive 73. The controller 70 is communicably connected to each of the projector 30, the projector moving mechanism 40, the camera 50, and the camera moving mechanism 60 described above. The controller 70 controls operations of these parts in accordance with computer programs. Accordingly, the processing for capturing an image of the biological sample 9 proceeds in the image capturing device 100.

As described above, according to the present embodiment, the image capturing device 100 and the well plate 1 that is set in the image capturing device 100 configure an image capturing system for acquiring an image of the biological sample 9.

3. Image Capturing Processing

When an image of the biological sample 9 is captured, first, the well plate 1 is set on the stage 20 of the image capturing device 100. In each well 10 of the well plate 1, the biological sample 9 is held together with the culture solution 91.

When the well plate 1 is set on the stage 20, the controller 70 operates the projector moving mechanism 40 and the camera moving mechanism 60. Accordingly, the projector 30 and the camera 50 are moved above and below the wells 10 to be captured. Then, the controller 70 operates the projector 30 and the camera 50 to capture an image of the biological sample 9 held in the wells 10. Specifically, the projector 30 emits illumination light downward, and the camera 50 captures an image. Accordingly, an image of the biological sample 9 held in the wells 10 is obtained.

Figure 5A:
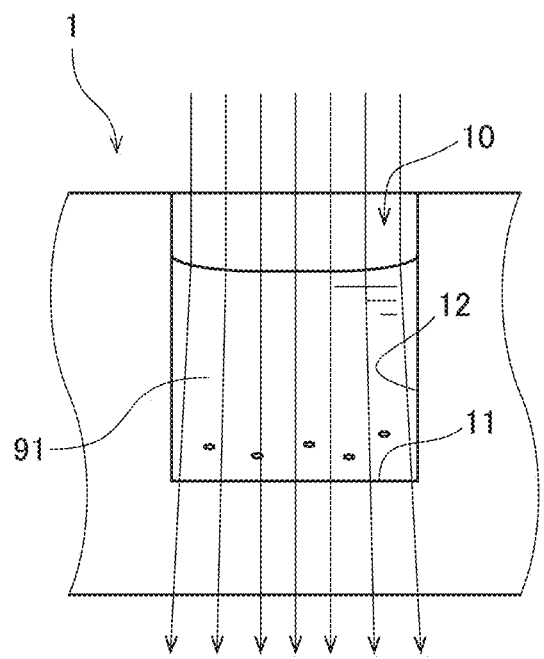
FIG. 5A is an illustration of illumination light incident on one well.
Figure 5B:
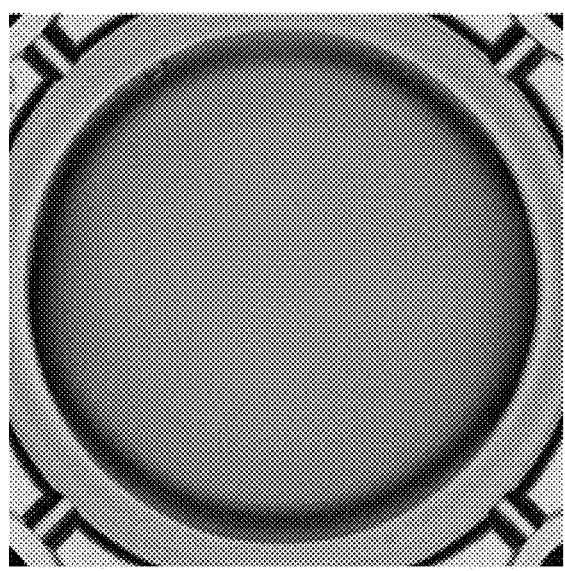
FIG. 5B shows an example of an image captured when the illumination light enters one well.
Figure 6A:
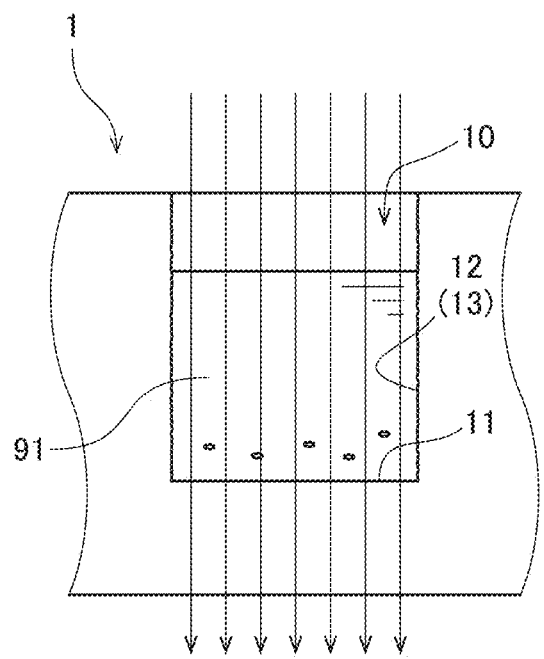
FIG. 6A is an illustration of illumination light incident on one well.
Figure 6B:
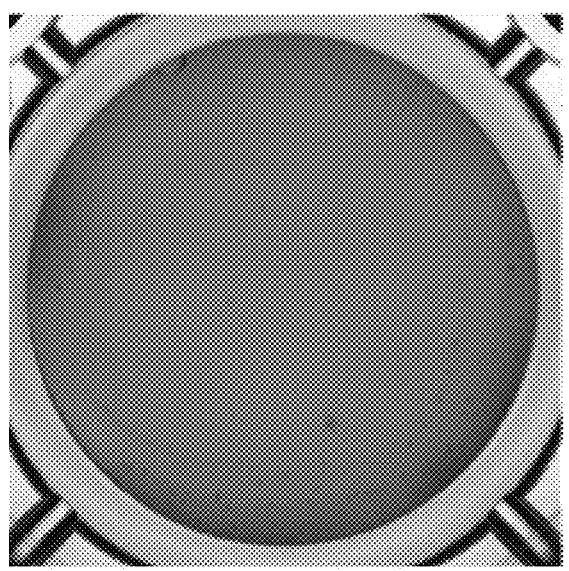
FIG. 6B shows an example of an image captured when the illumination light enters one well.

FIGS. 5A and 6A are illustrations of the illumination light incident on one well 10 during the image capture described above. FIGS. 5B and 6B show examples of the captured image when the aforementioned illumination light enters one well 10. FIGS. 5A and 5B show examples (comparative examples) for the case where the side surface 12 of the well 10 is not the rough surface 13. FIGS. 6A and 6B show examples (examples according to the present embodiment) for the case where the side surface 12 of the well 10 is the rough surface 13.

As illustrated in FIG. 5A, if the side surface 12 of the well 10 is not the rough surface 13, a meniscus is formed on the peripheral edge of the upper surface of the culture solution 91 due to surface tension of the culture solution 91. That is, the upper surface of the culture solution 91 is curved to form a concave shape. In this case, the illumination light incident on the peripheral edge of the upper surface of the culture solution 91 is refracted outward of the well 10 due to the effect of a concave lens of the culture solution 91. As a result, the peripheral edge of the well 10 becomes dark in the captured image obtained from the camera 50 as illustrated in FIG. 5B.

In contrast, if the side surface 12 of the well 10 is the rough surface 13 as illustrated in FIG. 6A, the rough surface 13 has the effect of water repellency. This is called the "Lotus effect," and microscopic asperities on the surface relate to this phenomenon. Based on experiences of the inventors of the present invention, water repellency suitable for observation is known to be achieved if the side surface 12 of the well 10 has arithmetic mean roughness Ra greater than or equal to 0.18 μm and less than or equal to 5.0 μm. In this case, the degree of the concave curve of the upper surface of the culture solution 91 is reduced, and the upper surface of the culture solution 91 becomes almost flat. This reduces the possibility that the illumination light incident on the peripheral edge of the upper surface of the culture solution 91 is refracted outward. As a result, it is possible to reduce the possibility that the peripheral edge of the captured image becomes dark in the image captured by the camera 50, as illustrated in FIG. 6B. Accordingly, the entire well 10 can have uniform brightness in the captured image.

Figure 7:
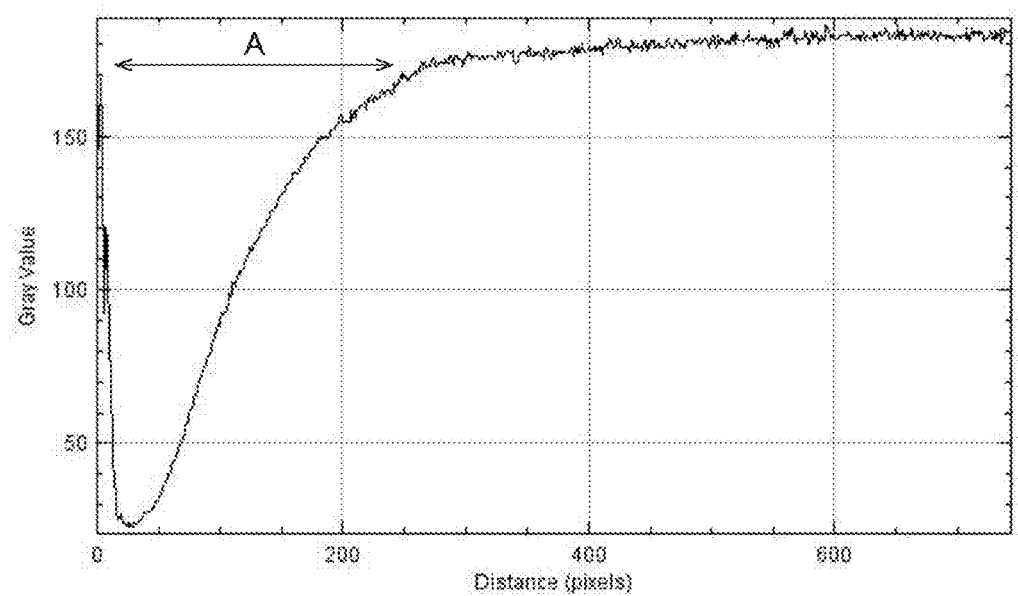
FIG. 7 is a graph showing the results of measuring luminance values in the vicinity of the peripheral edges of the wells in a captured image.
Figure 8:
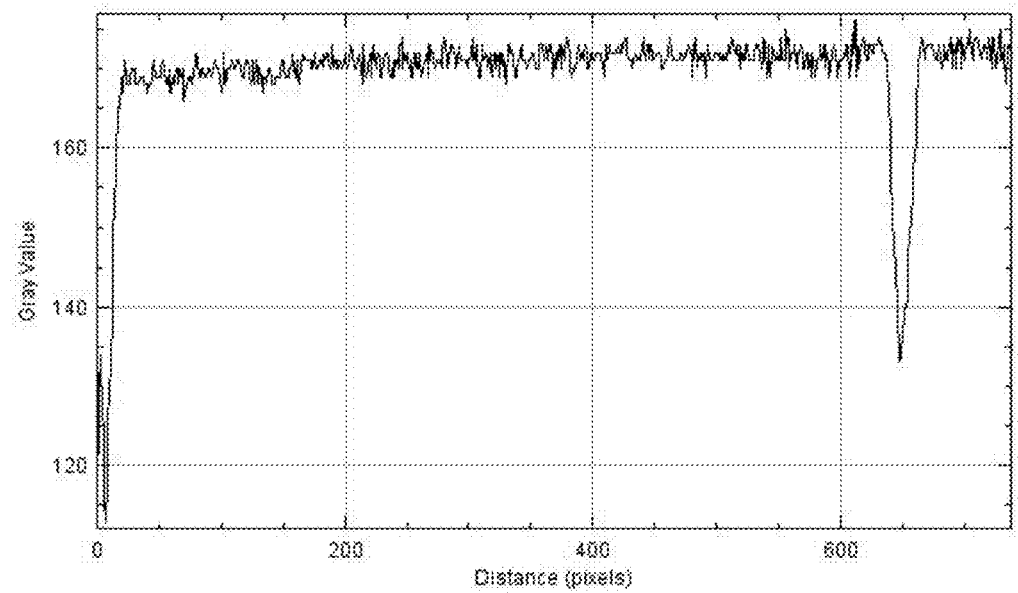
FIG. 8 is a graph showing the results of measuring luminance values in the vicinity of the peripheral edges of the wells in a captured image.

FIGS. 7 and 8 are graphs illustrating the results of measuring luminance values in the vicinity of the peripheral edge of the well 10 in an actual image captured by the camera 50. FIG. 7 shows an example (comparative example) for the case of using the well plate 1 whose side surface 12 is not the rough surface 13. FIG. 8 shows an example (example according to the present embodiment) for the case of using the well plate 1 whose side surface 12 is the rough surface 13. Conditions for measurement other than the side surface 12 of the well 10 are made equivalent. In FIGS. 7 and 8, the lateral axis indicates the distance from a predetermined position in the vicinity of the side surface 12 to the center of the well 10, and the longitudinal axis indicates the luminance value at that position.

In the example illustrated in FIG. 7, the luminance values decrease greatly in the vicinity of the peripheral edge of the well 10 (region A in FIG. 7) in the captured image. In contrast, the luminance values in the example illustrated in FIG. 8 do not decrease even in the vicinity of the peripheral edge of the well 10 in the captured image. This confirms that the rough surface 13 serving as the side surface 12 of the well 10 improves the luminance values in the vicinity of the peripheral edge of the well 10 in the captured image.

Figure 9:
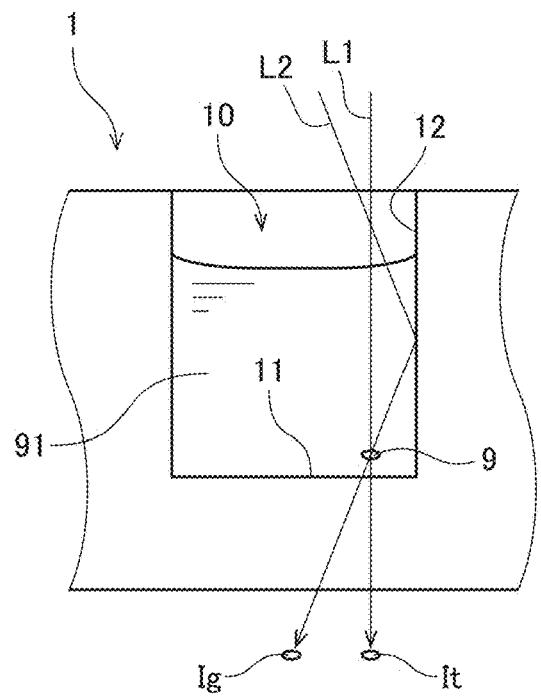
FIG. 9 is an illustration of part of illumination light incident on one well.
Figure 10:
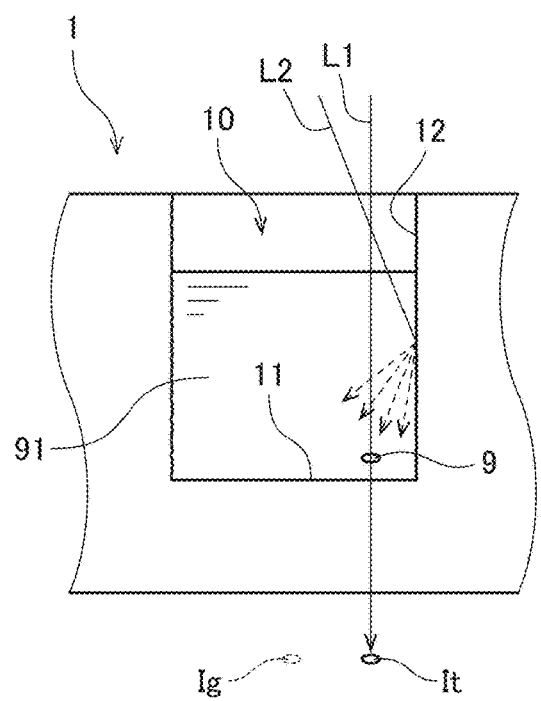
FIG. 10 is an illustration of part of illumination light incident on one well.

FIGS. 9 and 10 are illustrations of part of the illumination light incident on the well 10 during the image capture described above. FIG. 9 shows an example (comparative example) for the case where the side surface 12 of the well 10 is not the rough surface 13. FIG. 10 shows an example (example according to the present embodiment) for the case where the side surface 12 of the well 10 is the rough surface 13.

As illustrated in FIGS. 9 and 10, the illumination light emitted from the projector 30 includes not only primary illumination light L1 that travels vertically downward, but also secondary illumination light L2 that travels diagonally downward. Part of the secondary illumination light L2 enters the side surface 12 of the well 10. When the side surface 12 of the well 10 is not the rough surface 13 as illustrated in FIG. 9, the secondary illumination light L2 is mirror-reflected on the side surface 12. Thus, an image It of the biological sample 9 formed by the primary illumination light L1 and an image Ig (ghost) of the biological sample 9 formed by the aforementioned reflected light of the secondary illumination light L2 appear in the image captured by the camera 50.

In contrast, when the side surface 12 of the well 10 is the rough surface 13 as illustrated in FIG. 10, the secondary illumination light L2 incident on the rough surface 13 is diffused and reflected in a plurality of directions due to the presence of microscopic asperities on the rough surface 13. Thus, the amount of the secondary illumination light L2 reflected in the mirror reflection direction decreases. Accordingly, the image Ig (ghost) of the biological sample 9 formed by the reflected light of the secondary illumination light L2 is less likely to appear in the image captured by the camera 50. Since the amount of the primary illumination light L1 does not decrease, it is possible to reduce only the appearance of the image Ig (ghost) of the biological sample 9 formed by the reflected light of the secondary illumination light L2 in the captured image while maintaining clear appearance of the image It of the biological sample 9 formed by the primary illumination light L1.

Figure 11:
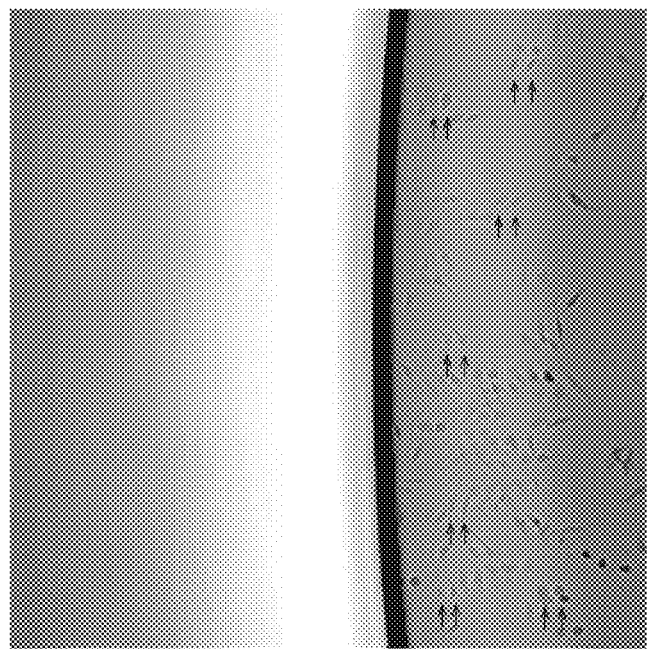
FIG. 11 shows an example of an image captured by a camera.
Figure 12:
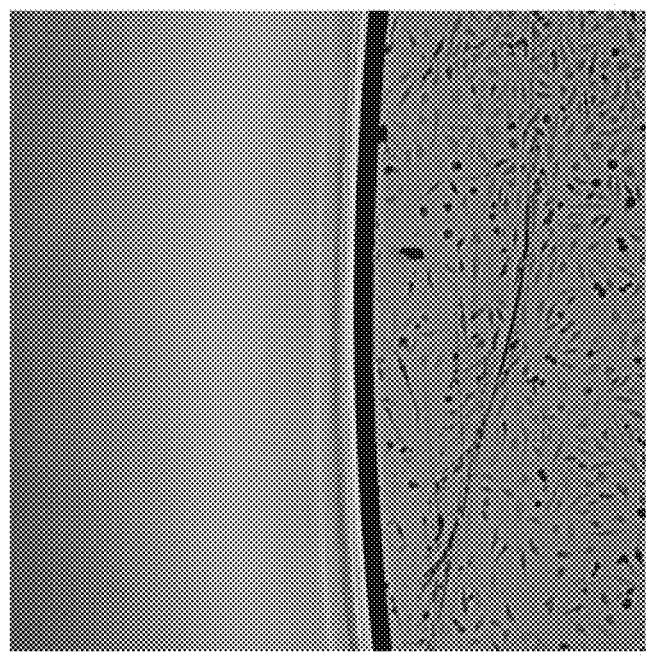
FIG. 12 shows an example of an image captured by the camera.

FIGS. 11 and 12 show examples of actual images captured by the camera 50. FIG. 11 shows an example (comparative example) for the case of using the well plate 1 whose side surface 12 is not the rough surface 13. FIG. 12 shows an example (example according to the present embodiment) for the case of using the well plate 1 whose side surface 12 is the rough surface 13. Conditions for image capturing other than the side surface 12 of the well 10 are made equivalent.

In the example illustrated in FIG. 11, double images of the biological sample 9 appear as indicated by arrows. This is considered due to appearance of both the image of the biological sample 9 formed by the primary illumination light L1 and the image of the biological sample 9 formed by the reflected light of the secondary illumination light L2. In contrast, in the example illustrated in FIG. 12, there are no portions in which double images of the biological sample 9 appear. This confirms that the rough surface 13 serving as the side surface 12 of the well 10 reduces the appearance of the image (ghost) of the biological sample 9 formed by the reflected light of the secondary illumination light L2.

4. Evaluation of Parameters Related to Rough Surface

The following results are obtained by changing three parameters including arithmetic mean roughness Ra, flaw width, and flaw spacing and making evaluations of water repellency of the rough surface 13 to the culture solution 91 by way of experiment.

Arithmetic mean roughness Ra (μm)
0 to 0.18: Poor
0.18 to 0.3: Good
0.3 to 0.5: Very good
Flaw width (μm)
0 to 25: Poor
25 to 110: Very good
Flaw spacing (μm)
30 to 50: Very good
50 to 60: Good
60 to 150: Poor In the above results, water repellency is classified into three levels: "Very good," "Good," and "Poor" depending on the area of droplets dropped on the rough surface 13. Here, "Good" indicates the smaller area of droplets than "Poor," and "Very good" indicates the yet smaller area of droplets than "Good."

Figure 13:
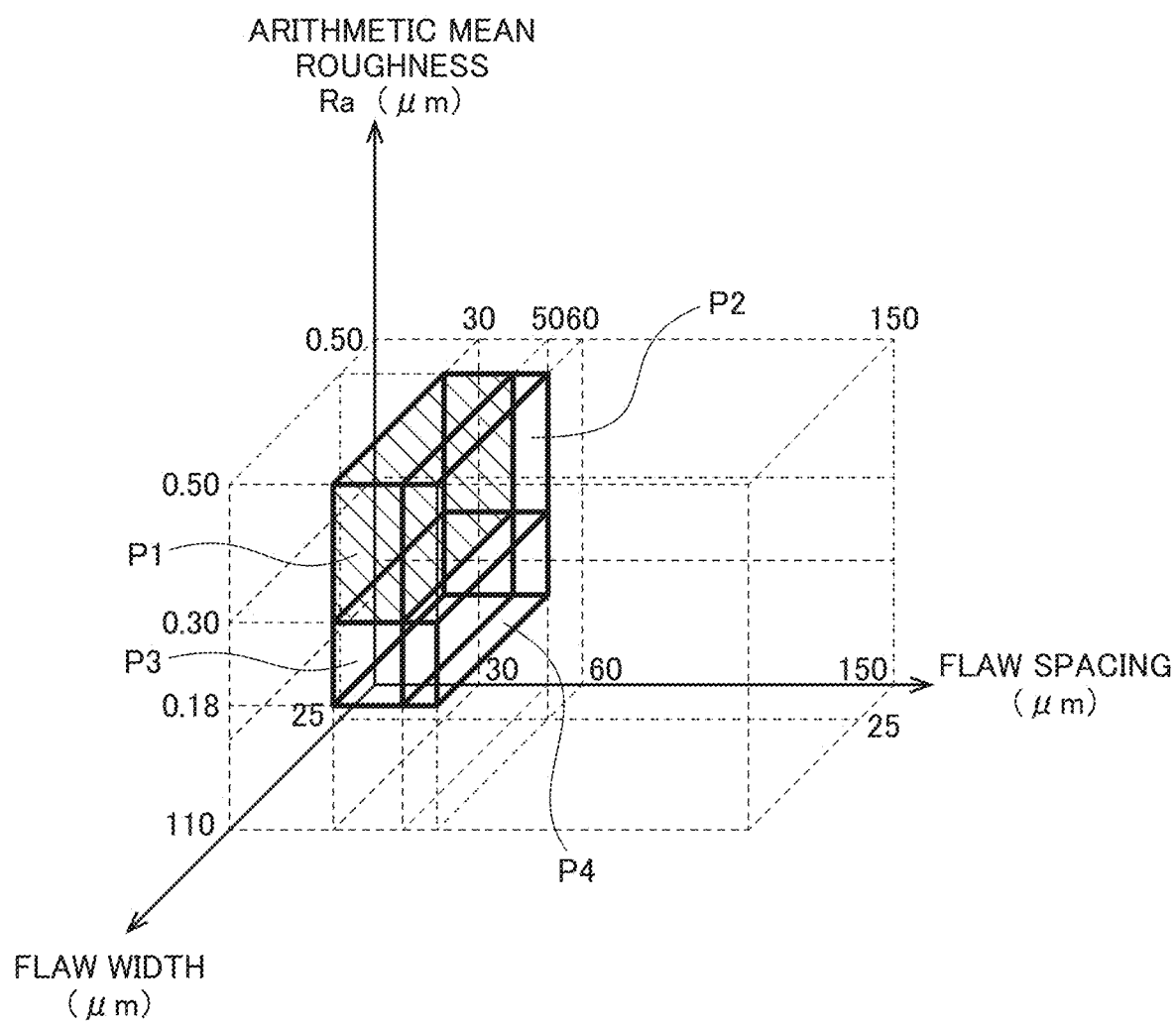
FIG. 13 is an illustration of the results of evaluating parameters regarding a rough surface.

FIG. 13 is an illustration of the above-described evaluation results represented in a coordinate system based on three axes: arithmetic mean roughness Ra, flaw width, and flaw spacing. The above-described results show that the most excellent water repellency is obtained under a condition of a region P1 (cross-hatched region in FIG. 13) with arithmetic mean roughness Ra of 0.3 to 0.5 μm, a flaw width of 25 to 110 μm, and a flaw spacing of 30 to 50 μm. The second most excellent water repellency is obtained under a condition of a region P2 with arithmetic mean roughness Ra of 0.3 to 0.5 μm, a flaw width of 25 to 110 μm, and a flaw spacing of 50 to 60 μm, or a region P3 with arithmetic mean roughness Ra of 0.18 to 0.3 μm, a flaw width of 25 to 110 μm, and a flaw spacing of 30 to 50 μm. The third most excellent water repellency is obtained under a condition of a region P4 with arithmetic mean roughness Ra of 0.18 to 0.3 μm, a flaw width of 25 to 110 μm, and a flaw spacing of 50 to 60 μm.

Note that among the above-described three parameters, in particular the arithmetic mean roughness Ra has a large influence on the effect of reducing meniscus formation in the culture solution 91 and the effect of reducing the possibility that an image (ghost) of the biological sample 9 is formed by the secondary illumination light. Thus, the numerical ranges of the flaw width and the flaw spacing are not absolute necessities for the present invention, and only the arithmetic mean roughness Ra greater than or equal to 0.18 μm and less than or equal to 5.0 μm is absolutely necessary.

5. Variations

While one embodiment of the present invention has been described thus far, the present invention is not intended to be limited to the embodiment described above.

Figure 14:
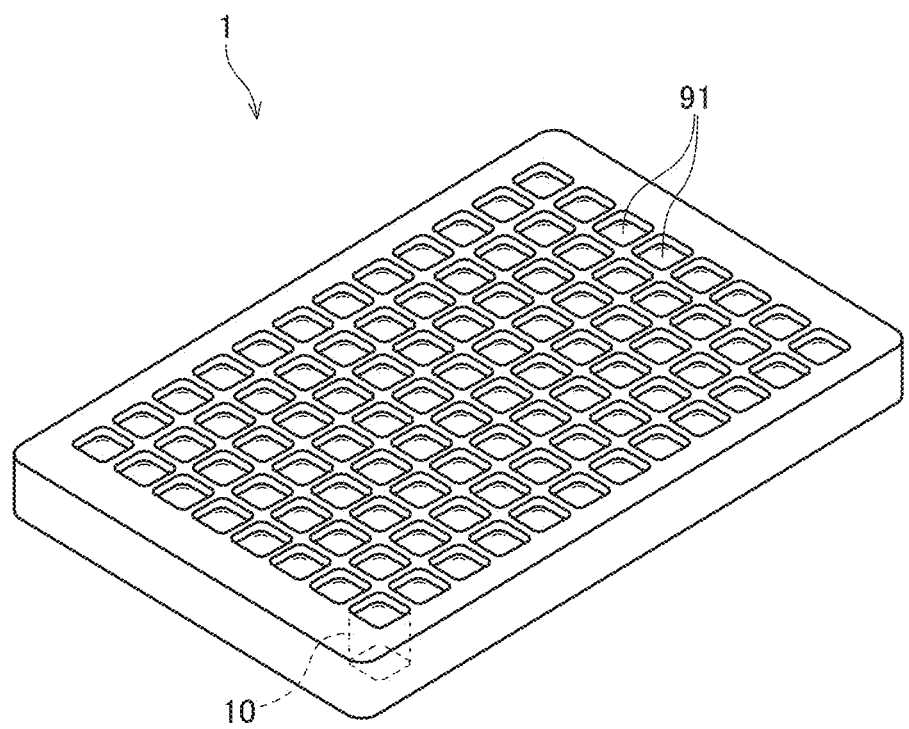
FIG. 14 is a perspective view of a well plate according to a variation.

In the embodiment described above, each well 10 of the well plate 1 has a circular shape when viewed from above. However, the shape of each well 10 may be a rectangle with round corners when viewed from above as illustrated in FIG. 14. If the side surface 12 of the well 10 of such a well plate 1 is not the rough surface 13, meniscuses in different conditions are formed between in the vicinity of the sides of the rectangle and in the vicinity of the corners of the rectangle on the peripheral edge of the upper surface of the culture solution 91. Thus, the amounts of luminance values reduced in the captured image also differ between the vicinity of the sides of the rectangle and the vicinity of the corners thereof. This results in the occurrence of dark portions with specific patterns in the captured image and thereby inhibits observation. Even if the wells 10 have such a rectangular shape, the rough surface 13 serving as the side surface 12 reduces meniscus formation on the upper surface of the culture solution 91. Accordingly, it is possible to reduce the occurrence of dark portions with specific patterns in the captured image.

An example in which the well plate 1 includes a plurality of wells (recesses) 10 is described in the above embodiment. However, the sample vessel according to the present invention may also be a share (petri dish) or flask with one recess. However, in the well plate 1, the influence of meniscus formation is relatively large because of a small size of each recess (e.g., with a diameter less than or equal to 10 mm). Accordingly, the application of the present invention to the well plate 1 particularly has significant technical meaning.

Although a case in which the camera 50 is used to capture and observe an image of the biological sample 9 held in the well plate 1 is described in the above embodiment, the well plate 1 may be used for visual observation of the biological sample 9 under epi-illumination without capturing an image of the biological sample 9 by the camera 50.

Each component according to the embodiment and the variations described above may be appropriately combined within the scope that does not cause any contradiction.

While the invention has been shown and described in detail, the foregoing description is in all aspects illustrative and not restrictive. It is therefore understood that numerous modifications and variations can be devised without departing from the scope of the invention.

What is claimed is:

1. A culture vessel for use in holding therein a biological sample together with a culture solution and observing said biological sample under epi-illumination, the culture vessel comprising:
   one or a plurality of recesses,
   wherein said one or a plurality of recesses each have:
      a flat bottom surface; and
      a side surface extending upward from a peripheral edge of said bottom surface, said side surface includes a rough surface, and
   said rough surface has arithmetic mean roughness greater than or equal to 0.18 μm and less than or equal to 5.0 μm.

2. The culture vessel according to claim 1, wherein said rough surface has a plurality of flaws, and
   said plurality of flaws have widths greater than or equal to 25 μm and less than or equal to 10 μm.

3. The culture vessel according to claim 1, wherein said plurality of flaws in said rough surface have a flaw spacing greater than or equal to 30 μm and less than or equal to 60 μm.

4. The culture vessel according to claim 1, wherein said rough surface has said arithmetic mean roughness in a longitudinal section.

5. The culture vessel according to claim 1, wherein said rough surface has asperities of different sizes distributed at random.

6. The culture vessel according to claim 1, wherein said rough surface is distributed all around said side surface.

7. The culture vessel according to claim 1, wherein said rough surface is distributed entirely from an upper end of said side surface to a lower end of said side surface.

8. The culture vessel according to claim 1, wherein said rough surface is a machined surface formed by sandblasting, grinding using a grinder with abrasive grains or micro-projections, pressing using a mold with projections and depressions, chemical etching, or plasma irradiation.

9. The culture vessel according to claim 1, being a well plate including a plurality of recesses, said plurality of recesses being said one or a plurality of recesses.

* * * * *